United States Patent [19]

Hencken et al.

[11] 4,441,816

[45] Apr. 10, 1984

[54] OPTICAL DOUBLE-SLIT PARTICLE MEASURING SYSTEM

[75] Inventors: Kenneth R. Hencken, Pleasanton; Daniel A. Tichenor, Freemont; James C. F. Wang, Livermore, all of Calif.

[73] Assignee: The United States of America as represented by the United States Department of Energy, Washington, D.C.

[21] Appl. No.: 361,954

[22] Filed: Mar. 25, 1982

[51] Int. Cl.³ ............................................. G01N 15/02
[52] U.S. Cl. ..................................... 356/335; 356/386
[58] Field of Search ............... 356/335, 336, 384, 385, 356/386; 250/237 R, 237 G, 222.2

[56] References Cited

U.S. PATENT DOCUMENTS

| | | |
|---|---|---|
| 2,969,708 | 1/1961 | Polanyi et al. |
| 3,028,544 | 4/1962 | Stone ............................. 356/386 X |
| 3,535,531 | 10/1970 | Neitzel |
| 3,797,937 | 3/1974 | Shofner |
| 3,830,569 | 8/1974 | Meric |
| 3,873,206 | 3/1975 | Wilcock |
| 4,037,964 | 7/1977 | Wertheimer et al. |
| 4,037,965 | 7/1977 | Weiss |
| 4,052,600 | 10/1977 | Wertheimer |
| 4,139,303 | 2/1979 | Carlson et al. |
| 4,188,121 | 2/1980 | Hirleman, Jr. et al. |

FOREIGN PATENT DOCUMENTS 2040443 8/1980 United Kingdom ................ 356/336

OTHER PUBLICATIONS

Bartholdi et al., "Differential Light Scattering Photometer ..." *Applied Optics*, vol. 19, No. 10, pp. 1573–1581, May 1980.

Wang et al., "Particle Size Measurements ...", *Applied Optics*, vol. 20, No. 8, pp. 1367–1373, Apr. 1981.

Fristrom et al., "Particle Sizing by Interference Fringes ...", *Faraday Symposia of the Chemical Society*, No. 7, pp. 183–197, 1973.

Oki et al., "A New Method for Evaluating the Size of Moving Particles ...", *Powder Technology*, vol. 11, pp. 51–57, 1975.

She et al., "Real-Time Particle Sizing Increasing the Capability ...", *Applied Optics*, vol. 14, No. 8, pp. 1767–1768, Aug. 1975.

Knollenberg, "Image Dissector for Size and Position ...", *Applied Optics*, vol. 18, No. 21, pp. 3602–3609, Nov. 1979.

*Primary Examiner*—William L. Sikes
*Assistant Examiner*—Matthew W. Koren
*Attorney, Agent, or Firm*—George H. Libman; James H. Chafin; Michael F. Esposito

[57] ABSTRACT

A method for in situ measurement of particle size is described. The size information is obtained by scanning an image of the particle across a double-slit mask and observing the transmitted light. This method is useful when the particle size of primary interest is 3 $\mu$m and larger. The technique is well suited to applications in which the particles are non-spherical and have unknown refractive index. It is particularly well suited to high temperature environments in which the particle incandescence provides the light source.

11 Claims, 5 Drawing Figures

OPTICAL DOUBLE-SLIT PARTICLE MEASURING SYSTEM

The U.S. Government has rights in this invention pursuant to Contract No. DE-AC04-76DP00789 between the U.S. Department of Energy and Western Electric Company.

BACKGROUND OF THE INVENTION

1. Field of the Invention

The invention is directed to a double-slit imaging system for measuring individual particle size, size distribution and particle velocity of particles suspended in a moving fluid. It is well suited for measuring particles of 3 μm and larger, for example, in situ measurements in fossil fuel combustion systems.

2. Description of the Prior Art

The several existing methods for making single particle measurements belong to one of three categories, i.e., scattering methods, imaging methods and interferometric methods.

The prior art with respect to imaging methods is, so far as is known, the following.

Wang et al., "Applied Optics", Vol. 20, pgs. 1367–1373 (Apr. 15, 1981) is directed to particle size measurement using an optical variable-frequency-grid technique. In the procedure described therein as the image of a particle scans across a variable frequency grid, the transmitted light signal oscillates with varying visibility. The visibility goes through a null at a well-defined point when the particle diameter approximates the local grid spacing. The optical configuration employed by the present system is also an imaging method and is generally similar to that of the variable-frequency-grid (VFG) system, the variable frequency grid being replaced by a double-slit mask. However, the signal obtained by the use of the double-slit mask is entirely different from that obtained by a variable-frequency-grid, i.e., a double-pulsed output signal instead of the null signal of said VFG system.

SUMMARY OF THE INVENTION

It is an object of the present invention to provide a new and improved method and apparatus for measuring individual particle size and size distributions of particles suspended in a moving fluid.

It is a further object to provide such a new and improved method and apparatus, as compared to prior art methods and apparatus, which has the following advantages:

(1) The optical system is very simple and of low cost.
(2) The signal from each particle is very simple, thus minimizing the complexity of the signal processing,
(3) The measurement volume is small, so that high particle densities can be accommodated,
(4) The size information is obtained from a single detector, so that the high optical sensitivity of photomultiplier tubes can be realized,
(5) Particle velocity, as well as size, can be measured,
(6) Incandescent particles can be measured using the particle itself as the light source,
(7) The size measurement is not subject to gross errors due to irregularity of particle shape as occurs in light-scattering methods; for non-spherical particles the parameter measured is approximately the length of the particle in the direction of travel,
(8) Knowledge of refractive index required in light-scattering methods is not required, and therefore the complexity of the system does not increase with uncertainty in refractive index.

In accordance with this invention, a method for measuring the size and velocity distribution of particles suspended in a moving fluid by the use of double-slit imaging systems is provided. In the preferred form of the invention, the light from incandescent particles is imaged by a lens system onto the double-slit mask so that it passes across both slits. The width of one of the mask slits is equal to or smaller than the smallest particle diameter of interest, and the width of the other slit is equal to or larger than the largest particle diameter of interest. Light passing from the particles through said mask is detected by a photomultiplier detector. The peak signals thereby generated by the photomultiplier detector can then be analyzed to yield the diameter and velocity of the suspended particles. If the particles are not incandescent, the particles must be illuminated by a separate light source.

The present invention further comprises a system for measuring the size and velocity distribution of particles suspended in a moving fluid. The preferred form of the system, when either incandescent or illuminated particles are to be subject of measurement, comprises: an imaging lens or system of lenses for focusing the light from the incandescent or illuminated particles into a double-slit mask as described above; a photomultiplier which receives the light signals from the double slit mask, and a display means which converts the signal data supplied from the photomultiplier into a visually observable double-pulsed signal. Additional components which are required when at least some of the particles to be measured can be out of focus in the sample volume comprise the following elements: a laser for generating a light beam which is focused at the center of the image of the large slit; a spectral filter that transmits only the laser wavelength to the double slit mask; and to a second photomultiplier, that reflects all other wavelengths.

DESCRIPTION OF THE PREFERRED EMBODIMENT

Figure 1:
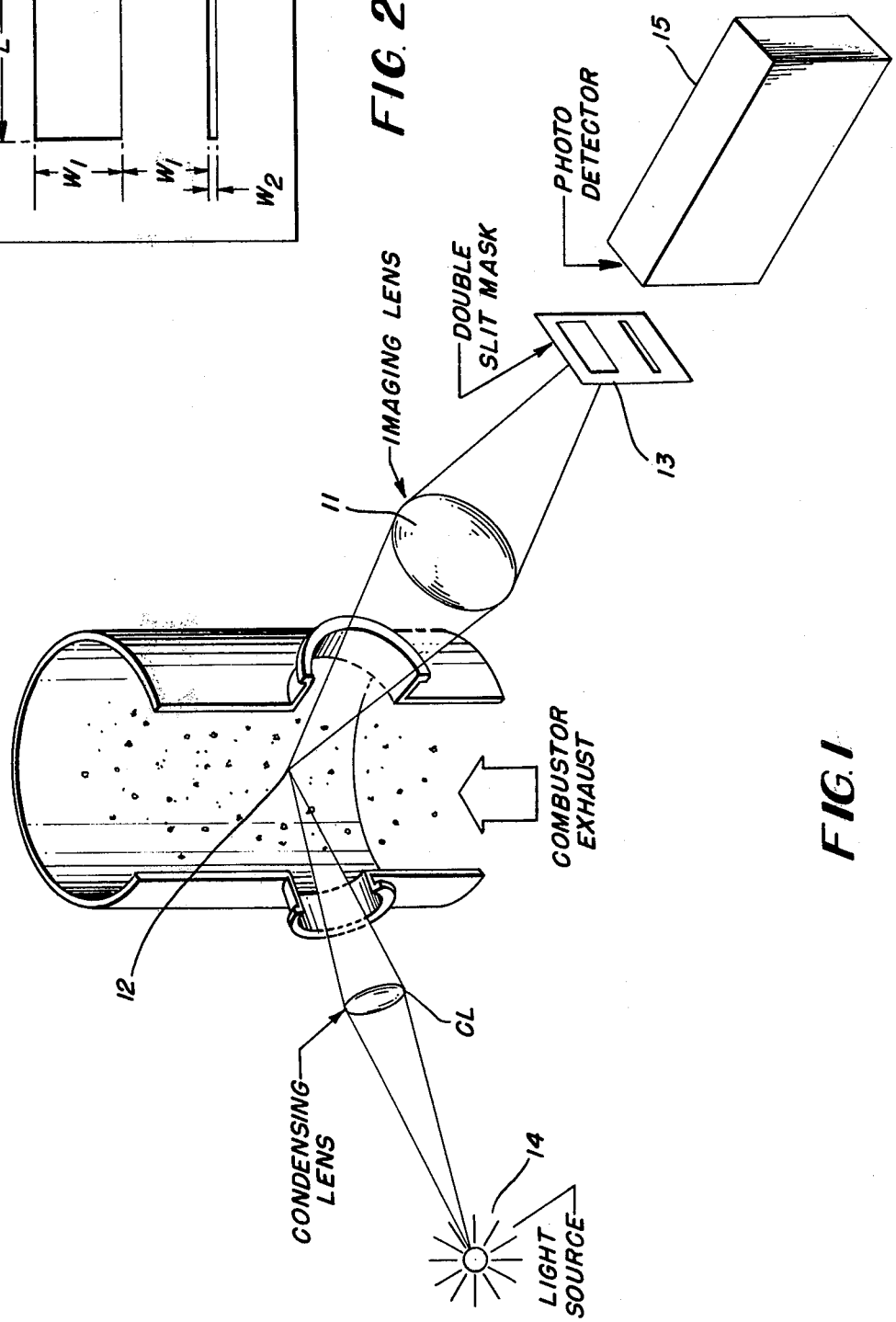
FIG. 1 is a partially block and partially pictoral diagram illustrating an apparatus, formed in accordance with the invention, wherein the size distribution of incandescent particles suspended in a moving fluid can be measured.

FIG. 1 shows an arrangement designed to measure non-luminous or luminous particles in situ in a combustor exhaust environment. As illustrated in FIG. 1, the system includes an imaging lens or system of lenses, which is arranged to image the lighting from incandescent particles 12 onto a double slit mask 13. For non-luminous particles, a light source 14 disposed at approximately a 90° angle from the imaging lens and focused through a condensing lens CL is provided. Light emitted from luminous particles or reflected from non-luminous particles passed through the slits of the mask 13 and to the photodetector 15, e.g., a photo-multiplier. The signals generated by the photomultiplier are passed to an electronic signal display device such as, for example, an oscilloscope (not shown) on which they are displayed as a double-pulsed signal.

Figure 2:
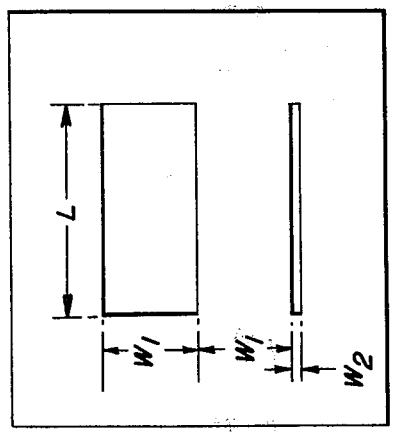
FIG. 2 is a dimensioned front view of a double-slit mask employed in the apparatus shown in FIG. 1.

FIG. 2 shows the details of the double-slit mask 13. The width $W_1$ of the upper slit is equal to or larger than the largest particle diameter of interest. The width $W_2$ of the lower slit is equal to or smaller than the diameter of the smallest particle of interest. The distance between slits $W_1$ and $W_2$ is equal to the width $W_1$ of the upper slit. The length L of each slit should be sufficiently large to eliminate edge effects, as will be described further hereinafter.

Figure 3A:
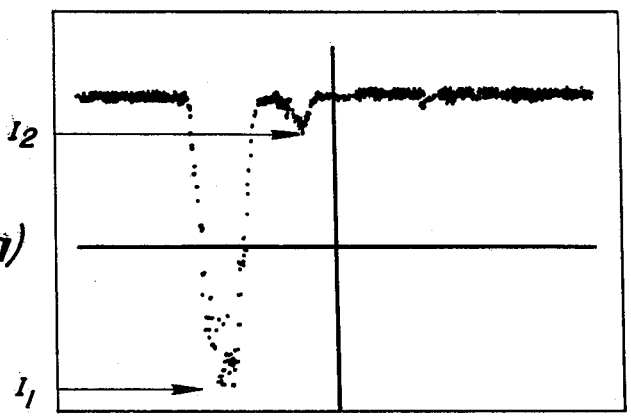
FIGS. 3(a) and 3(b) are graphs illustrating the double-pulsed signal visually shown on a display device which has converted the input signal data from a photomultiplier to form such a signal.
Figure 3B:
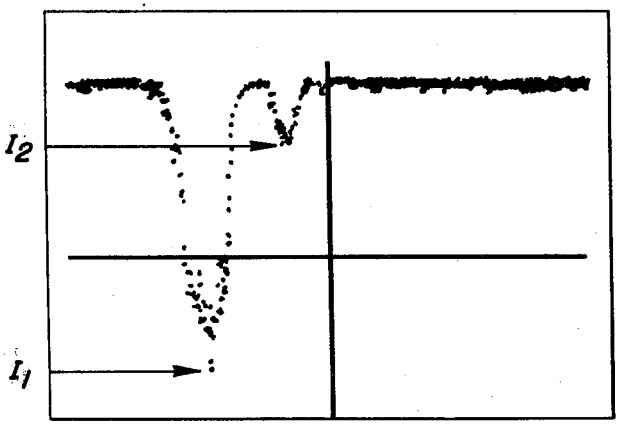

FIGS. 3(a) and 3(b) illustrate the typical double-pulsed signals which are generated by the photodetector 15 in FIG. 1 for 140 μm and 75 μm particles, respectively and displayed on a display device such as an oscilloscope. The peak signal $I_1$ is generated by the light passing through the upper slit $W_1$, and correspondingly the peak signal $I_2$ is generated by the light passing through the lower slit $W_2$, as the image of a particle 12 sequentially traverses slits $W_1$ and $W_2$.

Figure 4:
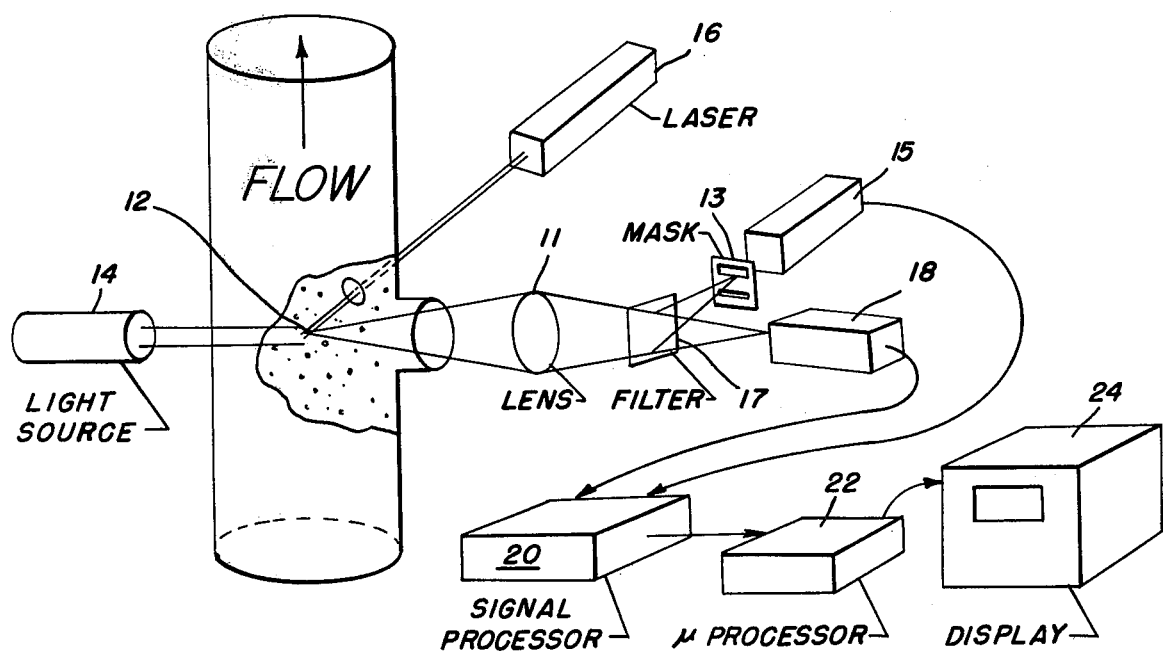
FIG. 4 is a partially block and partially pictorial diagram illustrating an apparatus, formed in accordance with the invention, wherein the size distribution of particles suspended in a moving fluid can be measured with special provisions for eliminating errors caused by out of focus particles in said moving fluid.

FIG. 4 shows a Schlieren imaging system similar in other respects to the system shown in FIG. 1, which has been discussed above, but provided with a beam stop at the center of the imaging lens and additional components to eliminate errors caused by out-of-focus particles. These additional components are a laser 16 which emits a beam to illuminate an in-focus particle 12. The scattered light from the particle passes through the imaging lens system 11 to the spectral filter 17 that transmits only the laser wavelength and reflects other wavelengths. The reflected light from the spectral filter is focused on the double-slit mask 13, while the laser beam is sent to a second photodetector 18.

This technique requires that an accurate image of each particle is cast onto the mask. To assure that only in-focus particles are evaluated, the laser 16, spectral filter 17 and the second photodetector 18 are required, the laser beam travels in the object plane of the lens 11 and is focused at the center of the image of slit $W_1$. Only particles within the depth-of-field of the imaging lens are illuminated. Since photodetector 18 sees mostly laser light transmitted by the spectral filter, a pulse from photodetector 18 will occur simultaneously with the first pulse from photodetector 15 for in-focus particles. Only signals from photodetector 15 that are coincident with a signal from photodetector 18 are processed, thereby eliminating defocusing errors.

In this regard, signal processor 20 contains a coincidence detector circuit which determines when signals are simultaneously detected by photodetectors 15 and 18; the lack of coincidence indicating an out-of-focus particle. Thus, only in-focus particles are processed. Also contained within signal processing circuit 20 are logarithmic amplifiers for generating the peak values $I_1$ and $I_2$ and digitizing the same.

A microprocessor 22 is provided to compute the particle diameter in accordance with the equations to be described hereinafter and to supply the signal and results related to the computations to the display device 24, such as an oscilloscope, to display a resulting histogram of the size distribution of particles being monitored. In further illustration of the operation of the invention, the following data is furnished.

EXAMPLE

An initial experiment was carried out to determine the feasibility of using this technique in a high temperature environment. Known-size alumina particles were injected into a methane/air flame. Most of the particles were confined to the focal region so that an external method of defining the sample volume was not required. Images of the particles were cast onto the mask using an f/8 lens. After following for the magnification (2.5×), the width of the narrow slit, $W_2$, was 13.3 μm and $W_1$ was 133 μm. The signals (FIG. 3) were digitized using a Nicolet Explorer III oscilloscope and processed in a PDP 11-34 computer. The two peak values $I_1$ and $I_2$ were determined and equation (3) to be described hereinafter as $$d \approx \frac{4}{\pi} W_2 \frac{I_1}{I_2},$$

was used to obtain particle size. This procedure was applied to a 192 double-pulsed signals to generate the histogram shown below.

| RATIO $I_1/I_2$ | PARTICLE SIZE | DISTRIBUTION OF RATIOS |
|---|---|---|
| Size distribution of incandescent alumina particles using a prototype Optical Double-Slit Particle Measuring System | | |
| 1.12 | 18.9 | |
| 1.22 | 20.8 | |
| 1.34 | 22.8 | |
| 1.47 | 25.0 | |
| 1.61 | 27.4 | |
| 1.77 | 30.0 | |
| 1.94 | 32.9 | |
| 2.13 | 36.1 | *** |
| 2.33 | 39.6 | |
| 2.56 | 43.4 | **** |
| 2.81 | 47.6 | ********* |
| 3.08 | 52.2 | ***** |
| 3.37 | 57.2 | ********** |
| 3.70 | 62.7 | ******************** |
| 4.06 | 68.8 | ********************* |
| 4.45 | 75.4 | *************** |
| 4.88 | 82.7 | ****************************** |
| 5.35 | 90.7 | ************** |
| 5.86 | 99.4 | ************* |
| 6.43 | 109.0 | **************** |
| 7.05 | 119.5 | ******** |
| 7.73 | 131.0 | *********** |
| 8.47 | 143.7 | ***** |
| 9.29 | 157.6 | ********* |
| 10.19 | 172.8 | ******* |

A discussion of the theory of operation of the invention as best understood in next set forth.

Stated in a general way, this system extracts image information, such as particle diameter, from a time signature S(t) generated by convolving the particle image P(x,y) with the mask 13 described by the transmittance function M(x,y), $$S(t) = \int_{-\infty}^{\infty} M(x,y) P(x,y - vt) \, dx \, dy,$$

where v is the particle velocity. In principle S(t) contains the size information for almost any choice of the mask. However, the mask should be chosen to simplify the process of obtaining size information from the resulting signal. In addition, the y dimension of the mask should be limited to minimize the sample volume. The Y dimension of the mask is the direction of particle movement and the X direction is perpendicular thereto.

These considerations resulted in the double-slit mask design shown in FIG. 2. The slits of widths $W_1$ and $W_2$ are separated by an opaque region of width $W_1$ such that $W_1$ is equal to the largest particle diameter of interest and $W_2$ is equal to the smallest particle diameter of interest. When the image of a moving particle 12 scans across the mask perpendicular to the slits the transmitted light is represented by a double-pulsed signal, such as illustrated in FIGS. 3(a) and 3(b).

Assuming the surface of the particle is Lambertian, the particle size can be extracted from the peak values of the two pulses. Let us first consider the back scatter configuration in which the illumination and viewing directions are approximately aligned. In this case the particle image is uniformly bright throughout the projection of the particle onto the image plane. Since the large slit $W_1$ is wider than the particle dimension, the first signal peak, $I_1$, is proportional to the projected area. The second pulse height, $I_2$, is proportional to $W_2$ times the horizontal dimension of the particle. For a spherical particle of diameter, d, where $W_2 < d < W_1$, the ratio $I_2/I_1$ is a monotonic function of d, $$\frac{I_2}{I_1} = \frac{4}{\pi} \frac{W_2}{d} \sqrt{1 - \left(\frac{W_2}{d}\right)^2} + \frac{1}{\pi}\left[\sin^{-1}\left(\frac{W_2}{d}\right) - \left(\frac{W_2}{d}\right)\right]. \quad (2)$$

This equation can be solved numerically for d. When $W_2 << d$ the approximate solution is $$d \approx \frac{4}{\pi} W_2 \frac{I_1}{I_2} \quad (3)$$

For non-spherical particles, the value obtained from equation (2) is approximately equal to the dimension of the particle measured in the direction perpendicular to the length of the narrow slit $W_2$.

A similar analysis can be performed for an arbitrary illumination angle. In the 90° illumination arrangement of FIG. 1 a spherical particle generates a half-moon image on the mask, and the resulting relationship between the pulse-height ratio and the particle diameter is also described by equations (2) and (3). In general, this relationship depends on illumination angle.

All of the above-described arrangements, like other single particle counters, are subject to errors when the particle passes through the edge of the sample volume. Two types of errors occur in the double-slit system. First, when a particle is out of focus, the measured diameter is greater than the true value. In the other case, the particle passes across the ends of the slits $W_1$ and $W_2$ may be over-sized and under-sized as a result.

Out-of-focus errors can be eliminated when off-axis illumination is used by simply confining the illumination beam to the in-focus region. In the other arrangements, an external method of defining the focal region must be used, unless, of course, the particle beam itself is confined to the focal region. These errors can be eliminated by illuminating the focal region with a monochromatic light source such as the laser 16 of FIG. 4 at right angles to the viewing directions. This wavelength is separated from the remaining light and detected by a second photodetector, as described hereinbefore. The resulting signal provides a coincidence check that allows only those particles passing through the in-focus region to be included in the histogram.

Edge effect errors can be handled in one of two ways. First, these errors can be corrected by aligning the coincidence detector to be sensitive only to particles that pass through the center of the mask. On the other hand, if the length, L, of the slits is sufficiently large, edge effects are not severe. A geometrical analysis of a spherical particle passing at right angles to the slits yields the following expression for the measured diameter, d, normalized by the true diameter:

$$d = \frac{\left[1 - \frac{1}{2\pi}(\theta - \sin\theta)\right]}{\frac{1}{2} + \frac{x}{d}} \quad (4)$$

where $\theta = 2\cos^{-1}(2x/d)$ and $-d/2 < x < d/2$. The parameter, x, is the position of the center of the particle relative to the edge with negative values representing a center outside of the slits. These equations apply to the back-scatter and the self-luminous arrangement in which a full disc is imaged onto the mask.

Edge effects are more severe for larger particles, since they have a greater probability of engaging the edge. For positive values of x (particles centered within the slits) the particle is oversized by a maximum of 7.3%. For negative values of x, the particle is undersized such that severe errors occur only for a small range of x. If the slit length $L = 2W_1$, edge-effect errors are less than 16% for 80% of the largest particles ($d = W_1$). An even larger fraction of smaller particles are sized to this accuracy. For all particle sizes, the edge-effect errors decrease with increasing slit length.

The system of the present invention may also be used to measured particle velocity, if desired. This can be accomplished by measuring the distance (time) between the leading edges of the pulses $I_1$ and $I_2$ of the oscilloscope trace, such as in FIGS. 3(a) and 3(b) and dividing that time into the known distance $2W_1$.

The present system is designed for measuring one particle per measurement volume at a time. This measurement volume is defined by the product of slit length L, laser beam width, and mask height ($2W_1 + W_2$). For example, in an environment containing particles of 100 μm and smaller, this system can operate at number densities as high as $10^5$ particles/cm$^3$.

It will be understod that various changes in the details, materials and arrangement of the parts, which have been described and illustrated in order to explain the nature of the invention, may be made by those skilled in the art within the principles and scope of the invention, as expressed in the appended claims.

I claim:

1. A method for measuring the size of particles in a certain size range moving along a path comprising the steps of:

(a) emitting a beam of light from a given particle in a particle-containing medium within said path;

(b) positioning a double-slit mask at the image plane of an optical focusing element located between said path and double-slit mask, the double-slit mask having a first slit of a width equal to or larger than the largest particle diameter of interest and a second slit spaced therefrom of a width equal to or smaller than the diameter of the smallest particle of interest;

(c) positioning a photodetector means at a location behind said double-slit mask;

(d) collecting with said optical-focusing element all of the light reflected from a given particle to form a particle image thereof and causing said image to scan periodically across the slits of the double-slit mask;

(e) measuring the light intensity transmitted through the slits of the double-slit mask by the photodetector means, and wherein the distance between said first and second slits is sufficient to cause said means to generate a double-pulsed output signal, first pulse being related to the amount of light transmitted by said particle image through said first slit and a second pulse being related to the amount of light passing through said second slit; and (f) determining a particle diameter from the relationship of the peak values of the respective pulses of the double-pulsed output signal.

2. A method for measuring the size of particles in a certain size range moving along a path comprising the steps of:

(a) emitting a first beam of light from a given particle in a particle-containing medium within said path;

(b) projecting a second beam of light having a wavelength other than that of said first beam of light from said given particle;

(c) positioning a double-slit mask at the image plane of an optical focusing system including a spectral filter capable of reflecting the wavelength of the first beam and of transmitting the wavelength of the second beam, said optical focusing system being located between said path and said double-slit mask, the double-slit mask having a first slit of a width equal to or larger than the largest particle diameter of interest, and a second slit spaced therefrom of a width equal to or smaller than the diameter of the smallest particle of interest;

(d) positioning a first photodetector means at a location behind said double-slit mask and positioning a second photodetector means at a location behind said spectral filter mask;

(e) collecting with said optical focusing element all of the light reflected from said given particle to form a particle image thereof and causing, by means of the spectral filter, the particle image of the first beam to scan across the slits of the double-slit mask and the particle image of the second beam to be detected by the second photodetector means;

(f) measuring the light of the first beam transmitted through the slits of the double-slit mask by the first photodetector means, and wherein the distance between said first and second slits is sufficient to cause said means to generate a double-pulsed output signal, a first pulse being related to the amount of light transmitted by said particle image through said first slit and a second pulse being related to the amount of light passing through said second slit.

3. A method as recited in claims 1 or 2, in which the particle diameter is determined from the formula:

$$\frac{I_2}{I_1} = \frac{4}{\pi} \frac{W_2}{d} \sqrt{1 - \left(\frac{W_2}{d}\right)^2} + \frac{1}{\pi}\left[\arcsin\left(\frac{W_2}{d}\right) - \left(\frac{W_2}{d}\right)\right]$$

wherein:
d = particle diameter
$W_2$ = width of said second slit
$I_2$ = peak intensity of said second pulse derived from light transmitted through slit of $W_2$
$I_1$ = peak intensity of said first pulse derived from light transmitted through said first slit.

4. A system for measuring the size of the particles in a certain size range moving along a path comprising:

(a) optical focusing means located between said path for forming an image and an image plane of a given particle moving along said path;

(b) a double-slit mask of opaque material located at the image plane of the optical focusing means, said double-slit mask having a first slit of a width equal to or larger than the largest particle of interest and a second slit spaced therefrom of a width equal to or smaller than the diameter of the smallest particle of interest;

and (c) a photodetector means disposed behind the double-slit mask and wherein the distance between said first and second slits is sufficient to cause said means to generate a double-pulsed output signal, a first pulse being related to the amount of light transmitted by said particle image through said first slit and a second pulse being related to the amount of light passing through said second slit.

5. A system as recited in claim 4, including a means for projecting a beam of light onto said given particle in the path of the particles of a certain size range.

6. A system as recited in claim 5, in which the optical focusing means is disposed at an angle of 90° with respect to the means for projecting a beam of light onto the path of the particles of a certain size range.

7. A system as recited in claim 4, including a means for displaying the signals generated by the photodetector means.

8. A system as recited in claim 7, in which said means for displaying signal is an oscilloscope.

9. A system for measuring the size of particles in a certain size range moving along a path comprising:

(a) laser means disposed so as to project a beam of light onto a given particle in the path of particles of a certain size range;

(b) optical focusing means forming an image in an image plane of said given particle;

(c) spectral filter means for transmitting light of the wavelength of the laser beam and reflecting light of other wavelengths;

(d) a double-slit mask located at the image plane of the optical focusing element and means in the reflecting path of the spectral filter means, said double-slit mask having first a first slit of a width equal to or larger than the largest particle of interest and a second split spaced therefrom of a width equal to or smaller than the diameter of the smallest particle of interest;

(e) first photodetector means disposed behind the double-slit mask and wherein the distance between said first and second slits is sufficient to cause said means to generate a double-pulsed signal from the light transmitted through the slits of the double-slit mask, a first pulse being related to the amount of light transmitted by said particle image through said first slit and second pulse being related to the amount of light passing through said second slit;

(f) second photodetector means for generating a signal from the laser beam transmitted through the spectral filter;

(g) coincidence circuit means for generating a coincidence signal when the signal from said first and second photodetectors are generated simultaneously; and (h) circuit means for comparing the amplitude of the first and second pulses in response to said coincidence signal.

10. A system as recited in claim 9, including a means for projecting a beam of light of a wavelength other than the laser beam into the path of particles of a certain size range.

11. A system as recited in claim 10, including a means for displaying the signals generated by the first photodetector means when a coincident signal is generated by said coincident circuit means.

* * * * *